US008583397B2

(12) United States Patent
Braillard

(10) Patent No.: US 8,583,397 B2
(45) Date of Patent: Nov. 12, 2013

(54) DEVICE FOR DETERMINATION OF THERMAL EXCHANGE COEFFICIENT AND ASSOCIATED METHOD

(75) Inventor: Olivier Braillard, Venelles (FR)

(73) Assignee: Commissariat a l'Energie Atomique et aux Energies Alternatives, Paris (FR)

(*) Notice: Subject to any disclaimer, the term of this patent is extended or adjusted under 35 U.S.C. 154(b) by 321 days.

(21) Appl. No.: 13/140,812

(22) PCT Filed: Dec. 22, 2009

(86) PCT No.: PCT/EP2009/067741
§ 371 (c)(1),
(2), (4) Date: Jun. 17, 2011

(87) PCT Pub. No.: WO2010/072758
PCT Pub. Date: Jul. 1, 2010

(65) Prior Publication Data
US 2011/0257951 A1 Oct. 20, 2011

(30) Foreign Application Priority Data

Dec. 23, 2008 (FR) ..................... 08 59027

(51) Int. Cl.
*G01K 1/00* (2006.01)

(52) U.S. Cl.
USPC ........................................ 702/130

(58) Field of Classification Search
USPC ........................................ 702/130
See application file for complete search history.

(56) References Cited

U.S. PATENT DOCUMENTS

| 3,913,378 A | 10/1975 | Hausler |
| 5,453,944 A * | 9/1995 | Baumoel ........................... 703/2 |
| 6,824,305 B1 | 11/2004 | Boyd et al. |

FOREIGN PATENT DOCUMENTS

FR 2266869 A 10/1975

OTHER PUBLICATIONS

Lee, P. S. et al., "Investigation of Heat Transfer in Rectangular Microchannels," International Journal of Heat and Mass Transfer, vol. 48, No. 9, Apr. 2005, pp. 1687-1704.
Braillard, O. et al., "Thermal Load Determination in the Mixing Tee Impacted by a Turbulent Flow Generated by Two Fluids at Large Gap of Temparature," 13th International Conference on Nuclear Engineering, Beijing, China, May 2005, ICONE13-50361, 8 pages.
International Search Report in PCT Application No. PCT/EP2009/067741, mailed Apr. 19, 2010.
International Preliminary Report on Patentability in PCT Application No. PCT/EP2009/067741, mailed Jan. 19, 2011.
French Search Report in French Application Serial No. FR 0859027, dated Sep. 2, 2009.

* cited by examiner

*Primary Examiner* — Aditya Bhat
(74) *Attorney, Agent, or Firm* — Nixon Peabody LLP

(57) ABSTRACT

A device for determining the thermal exchange coefficient between a fluid and a wall at a point $P_N$ of a surface of the wall in contact with the fluid, including a measuring device (DT) which measures at least two temperature values $T_{C1}$ and $T_{C2}$ of the wall and a temperature value $T_F$ of the fluid, and a computer for calculating, from the temperature values $T_{C1}$ and $T_{C2}$, a temperature value $T_p$ of the wall and a thermal flow $\Phi$ given by the following equation:

$$\Phi = -\lambda \text{grad} (T_{C1} - T_{C2}),$$

where $\lambda$ is the thermal conductivity of the wall, and for calculating, from the fluid temperature $T_F$, the average temperature $T_P$ and the thermal flow $\phi$ the thermal exchange coefficient h in the following form:

$$h = \Phi/(T_F - T_P).$$

10 Claims, 2 Drawing Sheets

DEVICE FOR DETERMINATION OF THERMAL EXCHANGE COEFFICIENT AND ASSOCIATED METHOD

CROSS REFERENCE TO RELATED APPLICATIONS OR PRIORITY CLAIM

This application is a National Phase of PCT/EP2009/067741, filed Dec. 22, 2009, entitled, "DEVICE FOR DETERMINING A HEAT TRANSFER COEFFICIENT, AND ASSOCIATED METHOD", and which claims priority of, French Patent Application No. 08 59027, filed Dec. 23, 2008, the contents of which are incorporated herein by reference in their entirety.

TECHNICAL FIELD AND PRIOR ART

The invention concerns a device for determining a thermal exchange coefficient and the associated method.

Knowledge of the thermal exchange coefficient between a fluid which flows in a pipe and the wall of the pipe is essential information, in the field of physics, to calculate the heat exchanges between the fluid and the wall.

In the industrial field the thermal exchange coefficient is commonly used, in design, to dimension the surfaces of the thermal exchangers and to calculate the quantities of thermal power transmitted by a fluid. In detection, knowledge of the thermal exchange coefficient can characterise a malfunction such as, for example, the appearance of an instance of desiccation, the appearance of cavitations or the presence of non-condensable gases.

The thermal exchange coefficient is not measured directly using a sensor. To determine it mathematical exchange correlation models are used (Colburn, Dittus-Bolter or Rosenhow models) which require the knowledge of certain characteristics of the fluid, such as speed, viscosity, temperature, etc.

The difficulty, or the impossibility, which there is in obtaining a thermal exchange coefficient using correlation models is manifested in many industrial applications such as, for example, blends of turbulent fluids with great temperature differences (thermal fatigue), the presence of non-condensable gases, the presence of singularities, for example when a wall is facing fluid vortices which may lead to desiccation.

The device for measuring the thermal exchange coefficient of the invention and the associated method respond in a particularly advantageous manner to industrial applications in which the exchange correlation models are unsuitable.

Systems for measuring heat flows using a pipe in which a fluid flows are also known in the general technological background of the invention. These are however not systems for determining thermal exchange coefficients.

French patent application FR 2 266 869, entitled "Appareil de mesure de l'encrassement d'une surface métallique à courant de liquid" ("Device for measuring soiling of a metal surface using a liquid current") discloses such a system. The metal part of which it is desired to measure the soiling of the surface is inserted in the wall of a pipe, with the soiled metal surface in contact with the liquid circulating in the pipe, and with the metal surface located opposite the soiled surface in contact with a heating resistor which heats the part. Two temperature sensors are positioned in the metal part, one close to the heating resistor and the other close to the liquid, with a third sensor positioned in the liquid, close to the surface. The two temperature sensors which are positioned in the metal part measure the temperature difference existing throughout the full thickness of the metal part, thereby characterising the thermal energy added by the heating resistor. The temperature sensor positioned in the liquid measures the temperature of the liquid close to the metal surface. The thermal resistance of the soiling and, consequently, the soiling itself are deduced from the difference of the temperature measurements between the metal part and the fluid.

Such a device is not a thermal exchange coefficient device. Indeed, a thermal exchange coefficient is measured passively, i.e. without any external addition of heat, which interferes with the measurement.

In addition, the measurement made concerns the soiling of the entire surface of the metal part. A measurement integrated over the entire surface of the metal part is thus obtained, not a local measurement.

In such a measurement system the man skilled in the art understands that, with regard to the positions of the various sensors, it is important:

a) that both measuring sensors which are positioned in the metal part are as far apart as possible, in an axis parallel to the thickness of the metal part (since one must be close to the heating resistor and the other close to the soiled surface), and b) that the measuring sensor positioned in the liquid is close to the soiled surface. The resulting measurement is not therefore a localised measurement, but an integrated measurement.

ACCOUNT OF THE INVENTION

The invention concerns a device for determining the thermal exchange coefficient between a fluid and a wall at a point $P_N$ of a surface of the wall in contact with the fluid, characterised in that it includes:

a temperature-measuring device which includes:

two wall temperature sensors, with a first temperature sensor measuring a first temperature value $T_{C1}$ of the wall at a point $P_1$ and a second temperature sensor measuring a second temperature value $T_{C2}$ of the wall at a point $P_2$ which is roughly aligned with point $P_1$ in a straight line normal to the surface at point $P_N$, and where point $P_1$ is the closer to the surface of the wall, and a fluid temperature sensor measuring a temperature value $T_F$ of the fluid at a point $P_F$ of the fluid roughly aligned with points $P_1$ and $P_2$, and a computer which includes:

first means for calculating, from the temperature values $T_{C1}$ and $T_{C2}$, a temperature value $T_p$ of the wall and a thermal flow $\Phi$ given by the following equation:

$$\Phi = -\lambda \mathrm{grad}\,(T_{C1} - T_{C2}),$$

where $\lambda$ is the thermal conductivity of the wall, and second means for calculating, from fluid temperature $T_F$, temperature $T_P$ and thermal flow $\Phi$ the thermal exchange coefficient h in the following form:

$$h = \Phi(T_F - T_P).$$

The temperature $T_p$ is calculated, for example, according to a reverse method based on the use of the flow determined at each instant. This method is presented in the document entitled "THERMAL LOAD DETERMINATION IN THE MIXING TEE IMPACTED BY A TURBULENT FLOW GENERATED BY TWO FLUIDS AT LARGE GAP OF TEMPERATURE" (Olivier Braillard, Yvon Jarny, Guillaume Balmigere; 13th International Conference on Nuclear Engineering; Beijing, China; 16-20 May 2005; ICONE 13-50361).

According to an additional feature of the invention, the temperature measuring device includes a third wall temperature sensor which measures a third temperature $T_o$ of the wall at a point $P_3$ roughly aligned with points $P_1$, $P_2$ and $P_F$, where point $P_3$ is further from point $P_N$ than point $P_2$.

The invention also concerns a method for determining the thermal exchange coefficient between a fluid and a wall at a point $P_N$ of a surface of the wall in contact with the fluid, characterised in that it includes:

a measurement of a first temperature value $T_{C1}$ of the wall at a point $P_1$, a measurement of a second temperature value $T_{C2}$ of the wall at a point $P_2$ roughly aligned with point $P_1$ in a straight line normal to the surface at the point $P_N$, where point $P_1$ is closest to the surface of the wall, a measurement of a temperature value $T_F$ of the fluid at a point $P_F$ of the fluid roughly aligned with points $P_1$ and $P_2$, a calculation of a temperature $T_P$ of the wall from the temperature values $T_{C1}$ and $T_{C2}$, a calculation of thermal flow $\Phi$ such that:

$$\Phi = -\lambda \operatorname{grad}(T_{C1} - T_{C2}),$$

where $\lambda$ is the thermal conductivity of the wall, and a calculation of the thermal exchange coefficient h such that:

$$h = \Phi(T_F - T_P)$$

According to an additional feature of the method of the invention, a third wall temperature measurement $T_{C3}$ is made at a point $P_3$ roughly aligned with points $P_1$, $P_2$ and $P_F$, where point $P_3$ is further from point $P_N$ than point $P_2$, and where temperature $T_{C3}$ is a temperature value used as a boundary condition for the calculation of the thermal exchange coefficient.

The invention is based on accurate local temperature measurements in a wall and in a fluid through an original sensor associated with a signal processing algorithm which calculates a set of physical magnitudes and determines by this means a local experimental thermal exchange coefficient between the wall and the fluid.

BRIEF DESCRIPTION OF THE FIGURES

Other features and advantages of the invention will appear on reading the preferential embodiment made in reference to the attached figures, among which.

In all the figures the same references designate the same elements.

DETAILED DESCRIPTION OF A PREFERENTIAL EMBODIMENT OF THE INVENTION

Figure 1:
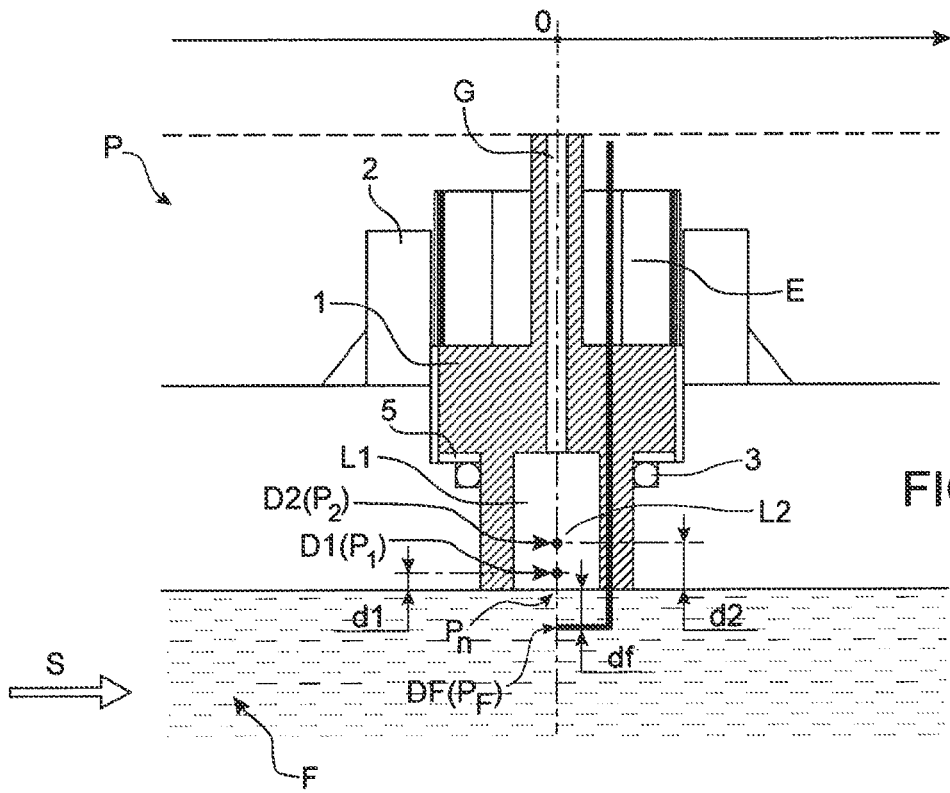
FIG. 1 represents a transverse section view of a first embodiment of a temperature measuring device forming part of a device for determining the thermal exchange coefficient in accordance with the invention.

FIG. 1 represents a transverse section view of a first embodiment of a temperature measuring device in accordance with the invention.

The temperature measuring device includes two temperature sensors D1, D2 positioned in the wall P and a temperature sensor DF positioned in the fluid F. Temperature sensors D1 and D2 are capable of sampling the temperature at respective points $P_1$ and $P_2$ of the wall, and temperature sensor DF is capable of sampling the temperature at a point $P_F$ of the fluid. Temperature sensors D1, D2 and DF are preferentially thermocouples the ends of which are positioned at the respective points $P_1$, $P_2$ and $P_F$. Points $P_1$, $P_2$ and $P_F$ are preferentially aligned in a straight line, at a point $P_N$, normal to the surface of the wall which is in contact with the fluid.

Temperature sensors D1, D2 and DF are positioned close to the surface of the wall P. Temperature sensor DF is aligned such that it faces the flow S of fluid F. Thermocouples D1 and D2 present in the wall P are attached in a cylindrical structure formed by the assembly of two half-moons L1, L2, and this structure is itself attached in a main body 1. The normal straight line in which points $P_1$, $P_2$ and $P_F$ are aligned coincides with the axis of the cylindrical structure formed by the half-moons L1, L2. Thermocouple DF is aligned facing the flow in order not to interfere with the latter. Thermocouples D1, D2 and DF have a diameter typically of between 20 gm and 200 μm. The diameters of the thermocouples are preferentially equal to 25 μm. Generally, the diameter of thermocouple DF is chosen with regard to the cutoff frequency which it is desired to attain. Thermocouple DF is located at a distance df from the surface of the wall P typically of between 10 μm and 1 cm, for example 2000 μm. Thermocouple D1, which is the one closest to the fluid, is positioned at a distance d1 from the surface of the wall P typically of between 10 μm and 3 mm, for example 300 μm, and thermocouple D2, which is the one furthest from the fluid, is positioned at a distance d2 from the surface of the wall P typically of between 100 μm and 1 cm, for example 500 μm.

Generally, thermocouple DF present in the fluid F must be, at the same time, sufficiently distant from thermocouples D1 and D2 which are positioned in the wall P in order not to interfere with the measurement of the thermal flow implemented by the method of the invention (cf. the method described below in reference to FIG. 3) and sufficiently close to these same thermocouples in order that a satisfactory correlation may be established between the fluid temperature measurement and the temperature measurements in the wall. The thermal conductivity of the wall is an essential parameter which is determining for the choices of the values given to the distances d1 and d2. In addition, for a given configuration of a measuring device of the invention as regards the distances df and d1, it has been shown that the correlation between the temperature $T_F$ of the fluid measured by the thermocouple $D_F$ and the wall temperature $T_{C1}$ measured by the thermocouple D1 closest to the fluid must be higher than a threshold in order to obtain a reliable thermal exchange coefficient calculation result. This correlation threshold may be equal, for example, to 80%. Below the correlation threshold there is uncertainty concerning the reliability of the result obtained. Advantageously, the method of the invention includes the calculation of a consistency function (cross-correlation function in the spectral representation) which estimates the uncertainty of the value of the calculated exchange coefficient.

The position of the main body 1 in the wall P and, hence, of thermocouples D1 and D2 relative to the fluid F, is mechanically adjusted using a shim 5. The main body 1 is attached to the chosen position once the face of the cylinder formed by the two half-moons which is in contact with the fluid is level with the inner surface of the wall P. A nut E helps attach the main body 1 in the wall P. Sealing is accomplished by means of an O-ring 3.

Before assembly the main body 1 and the two half-moons L1 and L2 are not yet either associated or positioned in the wall P, and the metal wires which constitute the two thermocouples D1 and D2 are preferentially covered with a fine layer of Kapton several microns thick (no magnesia and no sheath). Thermocouple DF is, conversely, a standard thermocouple fitted with an electrically insulating sheath.

The assembly of the measuring device includes, firstly, the formation of the measuring sensor and secondly the integration of the measuring sensor in the pipe.

The formation of the measuring sensor includes the following steps:

the wires which constitute both thermocouples D1 and D2 are passed into a sheath G formed in the main body 1, until these wires emerge beyond an open cavity formed in the main body;

the wires are positioned in routings previously made in a first of the two half-moons; the wires are attached in the routings of the first of the two half-moons (the bodies of the wires are attached by adhesive dots and the ends of the wires are attached by weld spots);

the thermocouple for measuring the temperature of the fluid DF is introduced in a through hole of very small diameter formed in the main body 1 until the end of the thermocouple emerges beyond the main body 1;

the second half-moon is attached facing the first half-moon so as to constitute a cylinder in which thermocouples D1 and D2 are inserted;

the cylinder thus formed is introduced in the open cavity formed in the previously mentioned main body 1 (for example by tight sliding fit) such that the cylinder formed by the two half-moons is level with the face of the main body demarcating the opening of the open cavity;

a seal weld is made of the joint formed by the two half-moons and the face of the main body 1;

the sealing of the thermocouple DF is accomplished in the place where it emerges from the hole made in the main body 1;

the thermocouple DF is folded back in a position intended to align it such that it is facing the flow of the fluid.

At this stage the construction of the sensor is complete and the integration of the sensor in the wall of the pipe is accomplished. Integration of the sensor includes the following steps:

the sensor is introduced into a cavity of wall P formed to this end, and the introduction of the sensor is accompanied by the positioning, in contact with wall P, of the shims 5 in order to adjust the position of the face of the sensor intended to be in contact with the fluid (the face of the sensor intended to be in contact with the fluid is thus positioned such that it is level with the inner surface of the wall P);

the sensor is sealed using the O-ring 3, since the fluid must not be introduced in the areas of the thermocouple welds; and the sensor is attached in wall P, for example using a nut E.

One advantage of the invention is that it provides a measuring device of very small dimensions, for example a volume of 0.2 cm$^3$, which is integrated in the pipe which it is desired to study, without any disturbance of the pipe due to this thermally non-intrusive integration. Furthermore, and also advantageously, the measuring device is entirely positioned on one side of the pipe, thus facilitating its integration.

Figure 2:
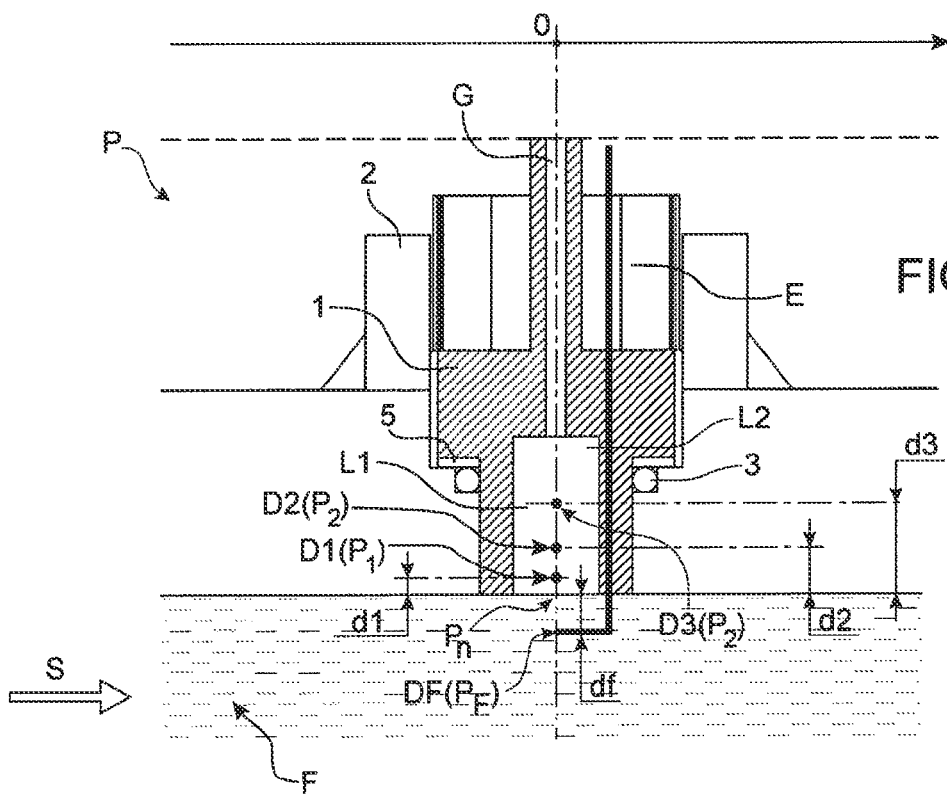
FIG. 2 represents a transverse section view of a second embodiment of a temperature measuring device forming part of a device for determining the thermal exchange coefficient in accordance with the invention.

FIG. 2 represents a temperature measuring device in accordance with a second embodiment of the invention. In addition to the elements previously described with reference to FIG. 1, the device of FIG. 2 includes an additional temperature sensor D3 inside the wall P. The function of temperature sensor D3 is to deliver a temperature which is used as a boundary condition in the calculations made by the computer C (cf. FIG. 3). The temperature delivered by the sensor D3 is then considered as the temperature of a semi-infinite wall. Sensor D3 is preferably a thermocouple the end of which P$_3$ is aligned with points P$_2$, P$_2$ and P$_F$. Sensor D3 is assembled in the measuring device at the same time as sensors D1 and D2. Due to its function, unlike the other sensors, temperature sensor D3 is not preferably positioned near the surface of the wall P in contact with the fluid. Sensor D3 is positioned at a distance d3 typically of between 1 mm and 3 cm from the fluid, for example 2.5 mm.

Figure 3:
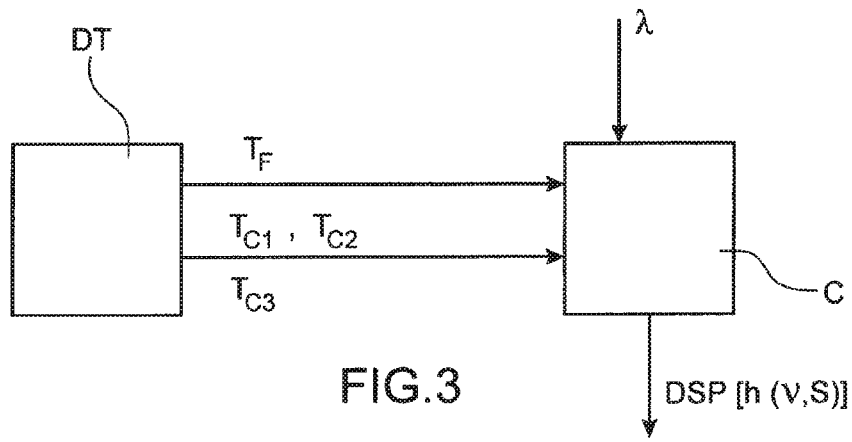
FIG. 3 represents an outline diagram of a device for measuring the thermal exchange coefficient in accordance with the invention.

FIG. 3 represents a schematic diagram of a device for determining the thermal exchange coefficient which uses the method of the invention. The device for determining the thermal exchange coefficient includes a temperature measuring device DT in accordance with the invention and a computer C which calculates the thermal exchange coefficient from the temperature measurements delivered by the device DT.

The method of the invention will firstly be described with reference to a measuring device DT in accordance with FIG. 1, in which only two temperature sensors D1 and D2 are present in the wall P.

At an instant t, the measuring device DT provides a fluid temperature measurement T$_F$ delivered by the sensor DF and two wall temperature measurements T$_{C1}$ and T$_2$ delivered by the respective sensors D1 and D2. The positions of the sensors are such that all the temperature measurements are taken roughly at the same abscissa s, where the axis of the abscissae is roughly perpendicular to the normal straight line in which points P$_1$, P$_2$ and P$_F$ are aligned. The temperatures T$_F$(t, s), T$_{C1}$(t, s) and T$_{C2}$(t, s) are transmitted to the computer C. From the temperatures T$_{C1}$(t, s) and T$_{C2}$(t, s), the computer C calculates the wall temperature T$_P$(t, s) and the thermal flow φ(t, s). The wall temperature T$_P$(t, s) is calculated, in a known manner, by the Becket method, and the thermal flow φ(t, s) is given by the following equation:

$$\Phi(t,s) = -\lambda \overrightarrow{\mathrm{grad}}(T_{C1}(t,s)T_{C2}(t,s)),$$

where λ is the thermal conductivity of the wall.

The thermal exchange coefficient (t, s) is then deduced using the following equation:

$$h(t, s) = \frac{\Phi(t, s)}{T_F(t, s) - T_P(t, s)}$$

At the output of the computer C the algorithm is thus able to supply, as a function of the time and the point considered of abscissa s of the wall P:

The temperature of the fluid (average and standard deviation);

The wall temperature in the area of sensor D1 (average and standard deviation);

The wall temperature in the area of sensor D2 (average and standard deviation);

The temperature of the wall (average and standard deviation);

The thermal exchange coefficient h (average and standard deviation).

In this first embodiment of the invention, in which only the two temperature sensors D1 and D2 are positioned in the wall P, the boundary conditions relative to the temperature are determined a priori, by every value considered as suitable for use.

The data delivered by the computer C is preferably expressed in the frequency domain. Thus, the computer C preferably delivers the power spectral density DSP[h(v,s)] from the Fourier transform of the exchange coefficient h(t, s).

The method of the invention then calculates the following expression for each frequency interval v:

$$DSP[h(v,s)] = \frac{DSP\Phi(v,s)}{DSP\Delta T(v,s)}$$

with $$DSP[\Delta T(v,s)] = DSP[T_F(t,s) - T_P(t,s)](v,s)$$

The algorithm provides an option according to which the determination of the power spectral density DSP[ΔT] is calculated by supposing that the measurement signals representative of the temperatures $T_F$ and $T_P$ have no phase-shifting (synchronous signals).

In this case, the power spectral density DSP[ΔT] is written as follows:

$$DSP[\Delta T(v,s)] = DSP[T_F(v,s)] - DSP[T_P(v,s)]$$

As was previously mentioned, the method of the invention calculates a consistency function, or spectral representation cross-correlation function, which estimates the uncertainty of the value of the exchange coefficient.

Figure 4:
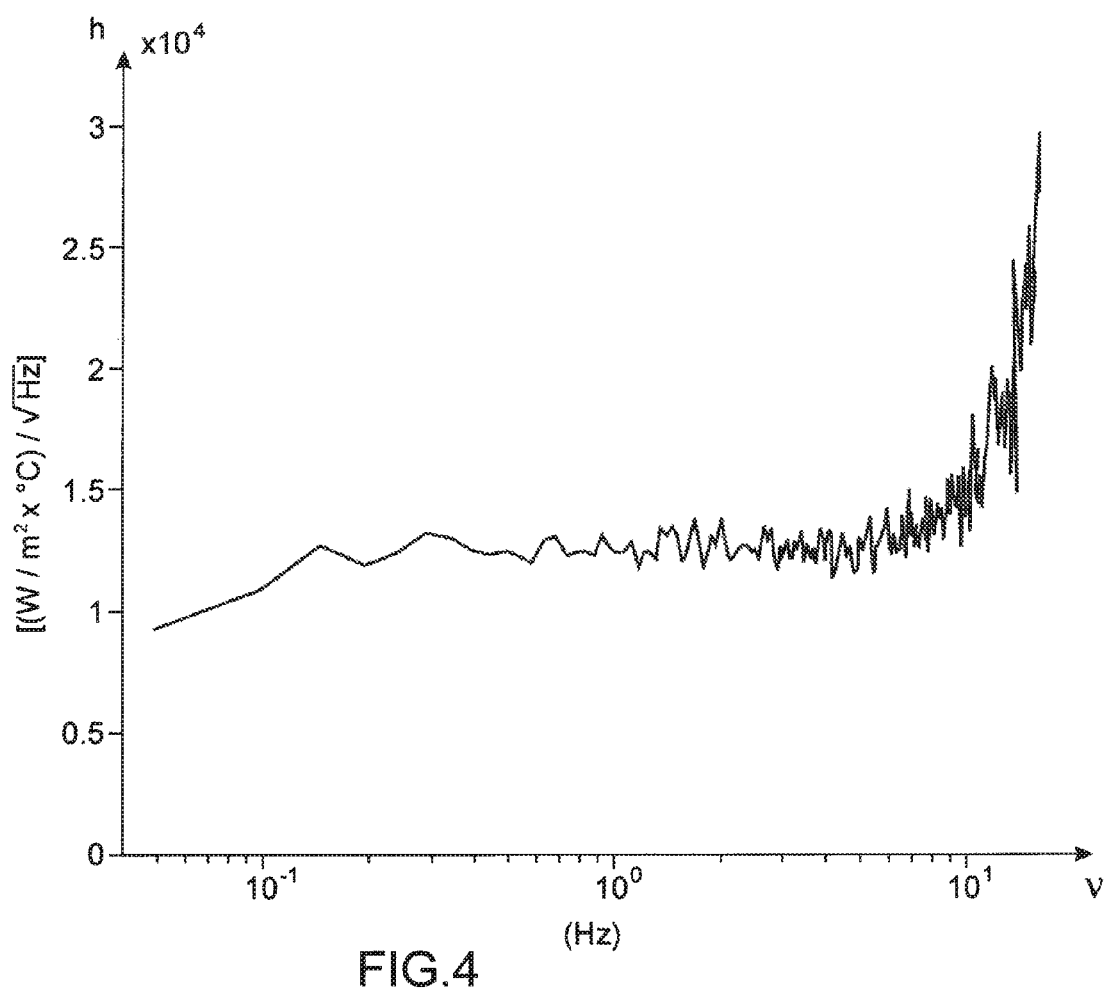
FIG. 4 represents an example of a thermal exchange coefficient power spectral density delivered by a device for determining a thermal exchange coefficient in accordance with the invention.

An example of a spectral power distribution of the exchange coefficient h is given in FIG. 4. The coefficient h(v) is expressed as $[(W/m^2 \times °C.)/\sqrt{Hz}] \times 10^4$. The conditions for obtaining the exchange coefficient of FIG. 4 are:

A sampling frequency equal to 50 Hz;
A start measurement frequency equal to 0.040 Hz;
An end measurement frequency equal to 10 Hz;
An analysis window size equal to 1024;
An acquisition time equal to 0.010 s;
An end of acquisition time equal to 900 s.

On the basis of the exchange coefficient represented in FIG. 4, the standard deviations Sigma(df) of the exchange coefficient h(v) can be calculated in relation to the frequency intervals df. This gives the following:

Sigma(≤1 Hz)=11922 W/m2×° C.;
Sigma(1 Hz-2 Hz)=12185 W/m²×° C.;
Sigma(2 Hz-3 Hz)=12521 W/m²×° C.;
Sigma(3 Hz-4 Hz)=12102 W/m²×° C.;
Sigma(4 Hz-5 Hz)=12286 W/m²×° C.;
Sigma(5 Hz-6 Hz)=12439 W/m²×° C.;
Sigma(6 Hz-7 Hz)=12880 W/m²×° C.;
Sigma(7 Hz-8 Hz)=12726 W/m²×° C.;
Sigma(8 Hz-9 Hz)=13691 W/m²×° C.;
Sigma(9 Hz-10 Hz)=14122 W/m²×° C.

The integration of the spectral power distribution by frequency bands advantageously enables the value of the thermal exchange coefficient h(v) to be situated easily, and also enables it to be known in which frequency band the thermal exchange is optimal.

The method of the invention will now be described in the case in which a third thermocouple D3 is positioned in the wall P. In this case the temperature $T_{C3}$ which is measured by the sensor D3 is used as a boundary condition in the calculations made by the computer C.

In addition, knowledge of the temperature $T_{C3}$ delivered by the sensor D3 advantageously enables, in addition to the flow Φ mentioned previously, the thermal flow $\Phi_a(t, s)$ to be calculated such that:

$$\Phi_a(s) = -\lambda\sqrt{\text{grad}}(T_{C1}(t,s) - T_{C3}(t,s))$$

The flows Φ(t, s) and $\Phi_a$(t, s) are then compared and, if these flows are roughly equal, it is possible to conclude that neither heat sinks nor heat sources are interfering with the measurement of the thermal flow. It is then said that a purely 1D situation has been attained.

Generally, the measuring device of the invention delivers local measurements (i.e. almost-punctual) which are average and fluctuating. Another advantage of the invention is, consequently, to allow establishment of a precise mapping of the thermal exchange coefficient on the basis of multiple measurements made, at different points, using different measuring devices.

The invention claimed is:

1. A device for determining the thermal exchange coefficient between a fluid (F) and a wall (P) at a point $P_N$ of a surface of the wall (P) in contact with the fluid (F), characterized in that it includes:
   a temperature-measuring device (DT) which includes:
   two wall temperature sensors (D1, D2), with a first temperature sensor (D1) measuring a first temperature value $T_{c1}$ of the wall at a point $P_1$ and a second temperature sensor (D2) measuring a second temperature value $T_{c2}$ of the wall at a point $P_2$ which is roughly aligned with point $P_1$ in a straight line normal to the surface at point $P_N$, and where point $P_1$ is the closer to the surface of the wall, and
   a fluid temperature sensor (DF) measuring a temperature value $T_F$ of the fluid at a point $P_F$ of the fluid roughly aligned with points $P_1$ and $P_2$, and
   a computer (C) which includes:
   first means for calculating, from the temperature values $T_{C1}$ and $T_{C2}$, a temperature value $T_p$ of the wall and a thermal flow Φ given by the following equation:

$$\Phi = -\lambda \text{grad}(T_{C1} - T_{C2}),$$

where λ is the thermal conductivity of the wall,
   and second means for calculating, from fluid temperature $T_F$, temperature $T_P$ and thermal flow Φ the thermal exchange coefficient h in the following form:

$$h = \Phi/(T_F - T_P).$$

2. A device according to claim 1, in which the temperature measuring device includes a third wall temperature sensor (D3) which measures a third temperature $T_{C3}$ of the wall at a point $P_3$ roughly aligned with points $P_1$, $P_2$ and $P_F$, where point $P_3$ is further from point $P_N$ than point $P_2$.

3. A device according to claim 2, in which the computer (C) includes third means for calculating, from the temperature values $T_{C2}$ and $T_{C3}$, an additional thermal flow $\Phi_a$ given by the following equation:

$$\Phi_a = -\lambda \text{grad}(T_{C2} - T_{C3}).$$

4. A device according to claim 1, in which each temperature sensor is a thermocouple.

5. A device according to claim 4, in which the thermocouples are positioned in a structure of cylindrical shape formed by an assembly of half-moons (L1, L2), where the straight line normal to the surface of the wall at the point $P_N$ is a central axis of the straight cylinder, and where a face of the straight cylinder in contact with the fluid is level with the surface of the wall.

6. A method for determining the thermal exchange coefficient between a fluid (F) and a wall (P) at a point $P_N$ of a surface of the wall (P) in contact with the fluid (F), characterized in that it includes:
   a measurement of a first temperature value $T_{C1}$ of the wall at a point $P_1$,
   a measurement of a second temperature value $T_{C2}$ of the wall at a point $P_2$ roughly aligned with point $P_1$ in a straight line normal to the surface at the point $P_N$, where point $P_1$ is closest to the surface of the wall, a measurement of a temperature value $T_F$ of the fluid at a point $P_F$ of the fluid roughly aligned with points $P_1$ and $P_2$, a calculation of an average temperature $T_P$ of the wall from the temperature values $T_{C1}$ and $T_{C2}$, a calculation of thermal flow $\Phi$ such that:

$\Phi = -\lambda \mathrm{grad}\,(T_{C1} - T_{C2})$, where $\Phi$ is the thermal conductivity of the wall, and a calculation of the thermal exchange coefficient h such that:

$h = \Phi/(T_F - T_P)$.

7. A method according to claim 6, in which the temperature $T_P$ is calculated by the Beck method.

8. A method according to claim 6, in which a third wall temperature measurement $T_{C3}$ is made at a point $P_3$ roughly aligned with points $P_1$, $P_2$ and $P_F$, where point $P_3$ is further from point $P_N$ than point $P_2$, and where temperature $T_{C3}$ is a temperature value used as a boundary condition for the calculation of the thermal exchange coefficient.

9. A method according to claim 8, in which the temperature $T_{C3}$ is used for a calculation of flow $\Phi_a$ such that:

$\Phi_a = \Phi \mathrm{grad}\,(T_{C2} - T_{C3})$.

10. A method according to claim 6, in which a consistency function is calculated which estimates an uncertainty of the calculated value of the thermal exchange coefficient.

\* \* \* \* \*